(12) United States Patent
Goodall et al.

(10) Patent No.: US 9,891,156 B2
(45) Date of Patent: Feb. 13, 2018

(54) METHOD FOR DETERMINING THE PERMEATION OF A PERMEANT THROUGH A MEMBRANE

(71) Applicant: Paraytec Limited, York, North Yorkshire (GB)

(72) Inventors: David Goodall, York (GB); Edmund Bergström, York (GB); Alexander Chapman, York (GB)

(73) Assignee: Paraytec Limited, York (GB)

( * ) Notice: Subject to any disclaimer, the term of this patent is extended or adjusted under 35 U.S.C. 154(b) by 0 days.

(21) Appl. No.: 15/324,330

(22) PCT Filed: Jul. 7, 2015

(86) PCT No.: PCT/GB2015/051963
§ 371 (c)(1),
(2) Date: Jan. 6, 2017

(87) PCT Pub. No.: WO2016/005735
PCT Pub. Date: Jan. 14, 2016

(65) Prior Publication Data
US 2017/0176314 A1   Jun. 22, 2017

(30) Foreign Application Priority Data
Jul. 9, 2014   (GB) .................................. 1412226.1

(51) Int. Cl.
*G01N 15/08* (2006.01)
*G01N 33/483* (2006.01)

(52) U.S. Cl.
CPC ....... *G01N 15/082* (2013.01); *G01N 15/0806* (2013.01); *G01N 33/483* (2013.01); *G01N 2015/0846* (2013.01)

(58) Field of Classification Search
CPC .................................................. G01N 15/082
See application file for complete search history.

(56) References Cited

U.S. PATENT DOCUMENTS

| | | | |
|---|---|---|---|
| 7,022,528 | B2 | 4/2006 | Avdeef et al. |
| 9,470,615 | B2 | 10/2016 | Graehlert et al. |
| 2003/0219716 | A1 | 11/2003 | Avdeef et al. |
| 2010/0225898 | A1 | 9/2010 | Lenke et al. |
| 2014/0223999 | A1 | 8/2014 | Graehlert et al. |

FOREIGN PATENT DOCUMENTS

| | | |
|---|---|---|
| DE | 102013002724 B3 | 7/2014 |
| WO | WO-03065037 A2 | 8/2003 |
| WO | WO-2008145115 A2 | 12/2008 |

OTHER PUBLICATIONS

Jesper Oostergaard et al: "Real-Time UV Imaging of Nicotine Release from Transdermal Patch", Pharmaceutical Research, Kluwer Academic Publishers-Plenum Publishers, NL, vol. 27, No. 12, Sep. 2, 2010 (Sep. 2, 2010), pp. 2614-1613.

(Continued)

*Primary Examiner* — David Porta
*Assistant Examiner* — Hugh H Maupin
(74) *Attorney, Agent, or Firm* — Harness, Dickey & Pierce, P.L.C.

(57) ABSTRACT

The present invention relates to a method of (and system for) characterizing the permeation of a permeant of interest between a first liquid or semi-solid and a second liquid across an interface (eg through a membrane) by using UV imaging.

5 Claims, 6 Drawing Sheets

(56) References Cited

OTHER PUBLICATIONS

Figure 1:
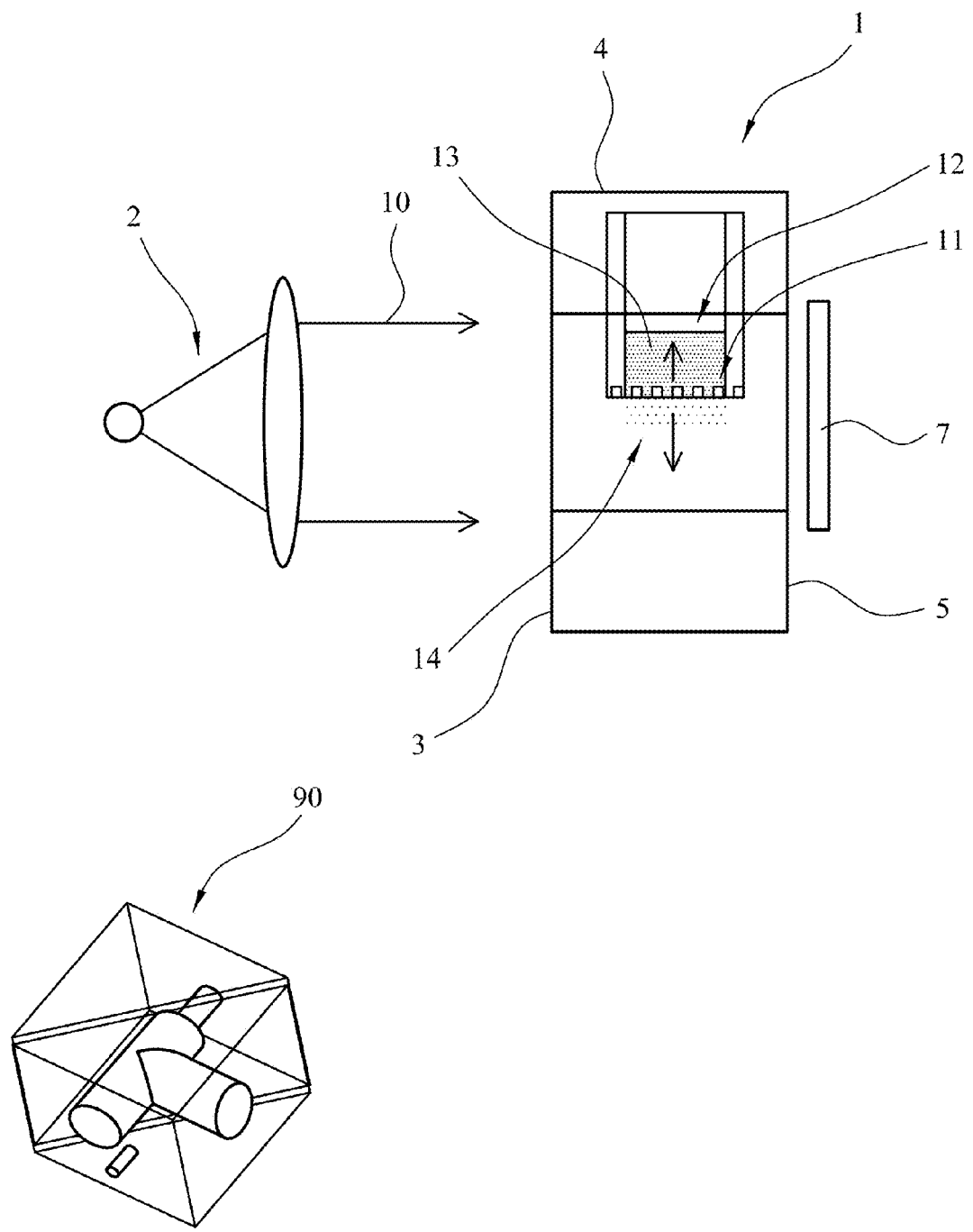

Kierstan et al, "UV-Spectrophotometry study of membrane transport processes with a novel diffusion cell," International Journal of Pharmaceutics, 229 (2001) 87-94.
Geninatti et al, Robotic UV-Vis apparatus for long-term characterization of drug release from nanochannels, Measurement Science and Technology 25 (2014) 027003 (6pp), IOPscience.iop.org.
Joshi et al, Transdermal Diffusion: In Vitro Diffusion Studies in Transdermal Research: A Synthetic Membrane Model in Place of Human Skin, Drug Development & Delivery, Mar. 2012, vol. 12, No. 2, pp. 40-42.
International Search Report and Written Opinion of the ISA for PCT/GB2015/051963, ISA/EP, Rijswijk, NL, dated Dec. 7, 2015.
British Search Report under Section 17 for priority application GB 1412226.1, dated Jan. 12, 2015.

(a)

(b)

METHOD FOR DETERMINING THE PERMEATION OF A PERMEANT THROUGH A MEMBRANE

CROSS-REFERENCE TO RELATED APPLICATIONS

This application is a 371 U.S. National Stage of International Application No. PCT/GB2015/051963, filed Jul. 7, 2015, which claims the benefit of and priority to British Patent Application No. 1412226.1, filed Jul. 9, 2014. The disclosures of the above applications are incorporated herein by reference.

The present invention relates to a method of (and system for) generating a representation of a characteristic of the permeation of a permeant of interest between a first liquid or semi-solid and a second liquid across an interface (eg through a membrane), to a sample assembly for containing a sample of the first liquid or semi-solid and the second liquid which comprises an elongate substantially planar holder, to the elongate substantially planar holder per se and to its use.

Current methods for in vitro release testing (IVRT) of semi-solid formulations in pharmaceuticals, biopharmaceuticals, cosmetics and personal care products are slow, resource intensive and require large amounts of sample. The current methodology approved by the regulatory agencies uses a Franz diffusion cell. Experiments typically take 6 hours to complete. Milliliter sample volumes are required and the experiments involve sampling of the receptor layer for high performance liquid chromatography (HPLC) analysis.

Kierstan et al, International Journal of Pharmaceutics, 229 (2001), 87-94 reported a UV spectrophotometric study of membrane transport processes. A diffusion cell and a diode array spectrophotometer allowed continuous monitoring of changes in the concentration of multiple species in the receiver compartment without sampling. The results were comparable with the performance of a Franz diffusion cell.

Geninatti et al, Measurement Science and Technology, 25 (2014), 1-6 reported a UV-VIS apparatus for characterising drug release from nanochannel membranes. Absorbance measurements of the release reservoir were collected to determine the amount of an analyte released through the nanochannel membrane.

The present invention seeks to improve the characterisation of the permeation of a permeant of interest across an interface (eg through a membrane) by monitoring directly the phase in which the permeant of interest is formulated. In particular, the present invention relates to monitoring a donor phase (eg a semi-solid donor phase) in which the permeant of interest is formulated using an ultra-violet area detector.

Thus viewed from a first aspect the present invention provides a method for generating a representation of a characteristic of the permeation of a permeant of interest between a first liquid or semi-solid and a second liquid across an interface therebetween, wherein the permeant of interest is formulated in either the first liquid or semi-solid or in the second liquid, wherein the method comprises:
  (A) providing a source of ultra-violet irradiation which is capable of generating ultra-violet irradiation along a path of incident ultra-violet irradiation;
  (B) containing a sample of the first liquid or semi-solid and the second liquid separated by the interface in a sample assembly positioned downstream in the path of incident ultra-violet irradiation such that there is a path length throughout an area of the sample, wherein the area of the sample is or includes an area of the first liquid or semi-solid or of the second liquid in which the permeant of interest is formulated;
  (C) generating ultra-violet irradiation from the source of ultra-violet irradiation along the path of incident ultra-violet irradiation whereby the incident ultra-violet irradiation is incident on the area of the sample;
  (D) detecting ultra-violet irradiation transmitted through or reflected from the sample spanning the area of the sample using an ultra-violet area detector; and
  (E) manipulating the ultra-violet irradiation transmitted through or reflected from the sample spanning the area of the sample into the representation of a characteristic of the permeation.

The method according to the invention may be faster, simpler and require less sample than conventional methods for characterising permeation. For example, the volume of the sample is typically one tenth of the volume of a sample required in a Franz diffusion cell and results are available in minutes rather than hours. From the representation may be advantageously deduced useful information relating to a system (eg an in vivo system) for which the sample is a mimic or simulant.

Where a semi-solid is self-supporting for a sustained period, the interface may be the physical boundary between the semi-solid and the second liquid. However in a preferred embodiment, the interface is a membrane between the first liquid or semi-solid and the second liquid.

In step (B), the sample or a part thereof (eg the first liquid or semi-solid) may be contained in the sample assembly as a 2D section or slice (eg in the XZ plane) such that the depth (Y) defines the path length thereof.

Preferably in step (B), the path length is substantially uniform throughout the area of the first liquid or semi-solid or of the second liquid in which the permeant of interest is formulated.

In a preferred embodiment, the permeant of interest is formulated in the first liquid or semi-solid and the area of the sample is or includes an area of the first liquid or semi-solid. Particularly preferably the area of the sample is or includes an area of the first liquid or semi-solid and of the second liquid.

Preferably the area of the sample includes an area of the membrane.

The area of the sample may include a first sub-area of the first liquid or semi-solid or of the second liquid in which the permeant of interest is formulated which contains substantially no permeant of interest. The transmitted or reflected ultra-violet irradiation spanning the first sub-area detected in step (D) may be used for referencing purposes.

The sample assembly may be positioned downstream in the path of incident ultra-violet irradiation such that there is additionally a path length throughout a second area outside the sample, wherein the incident ultra-violet irradiation is additionally incident on the second area. The transmitted or reflected ultra-violet irradiation spanning the second area detected in step (D) may be used for referencing purposes.

During the method of the invention, the second liquid may be stationary or agitated.

In a preferred embodiment, steps (D) and (E) are:
  (D) detecting ultra-violet irradiation transmitted through the sample spanning the area of the sample using an ultra-violet area detector; and
  (E) manipulating the ultra-violet irradiation transmitted through the sample spanning the area of the sample into the representation of a characteristic of the permeation.

In this embodiment, the ultra-violet irradiation transmitted through the sample spanning the area of the sample detected in step (D) is typically processed to the absorbance.

In a preferred embodiment, the source of ultra-violet irradiation is a source of ultra-violet and visible irradiation capable of generating visible irradiation along a path of incident visible irradiation and the ultra-violet area detector is an ultra-violet and visible area detector, wherein the method further comprises:

(C') generating visible irradiation from the source of ultra-violet and visible irradiation along the path of incident visible irradiation whereby the incident visible irradiation is incident on the area of the sample;

(D') detecting visible irradiation transmitted through or reflected from the sample spanning the area of the sample using the ultra-violet and visible area detector; and (E') manipulating the visible irradiation transmitted through or reflected from the sample spanning the area of the sample into the representation of a characteristic of a physical phenomenon.

Typically steps (C) and (D) are alternated with steps (C') and (D'). This may be achieved using an oscillating filter holder.

In an alternative preferred embodiment, the method further comprises:

(A") providing a source of visible irradiation which is capable of generating visible along a path of incident visible irradiation, wherein the source of visible irradiation is separate from the source of ultra-violet irradiation;

(C") generating visible irradiation from the source of visible irradiation along the path of incident visible irradiation whereby the incident visible irradiation is incident on the area of the sample;

(D") detecting visible irradiation transmitted through or reflected from the sample spanning the area of the sample using a visible area detector; and (E") manipulating the visible irradiation transmitted through or reflected from the sample spanning the area of the sample into the representation of a characteristic of a physical phenomenon.

Typically steps (C) and (D) are alternated with steps (C") and (D"). This may be achieved by switching.

The physical phenomenon may be a change to an interface or boundary or the generation or movement of a bubble.

The path of incident visible irradiation is typically coincident with the path of incident ultra-violet irradiation The characteristic of the permeation may be temporal, spatial, functional (eg mechanistic) or structural.

The representation of a characteristic of the permeation may be an image or a plurality of images (eg a plurality of images over a period of time such as a movie).

The representation of a characteristic of the permeation may be qualitative or quantitative. The representation of a characteristic of the permeation may be a visual, numerical or graphical representation. The representation of a characteristic of the permeation may be a chemical or physical parameter.

The representation of a characteristic of the permeation may be an absorbance profile (eg a difference absorbance profile).

Preferably the representation of a characteristic of the permeation is the depletion release profile in the semi-solid or first liquid and optionally the cumulative release profile in the second liquid.

Preferably the characteristic of the permeation is release rate over a period of time (eg $\mu g/cm^2 \cdot \sqrt{hr}$), flux (eg $\mu g/cm^2 \cdot hr$) or permeability (eg cm/hr).

The permeant of interest may be an active pharmaceutical ingredient (API), an active biopharmaceutical ingredient, a biocide, a diagnostic agent or a cosmetic agent.

Preferably the permeant of interest is an active pharmaceutical ingredient.

Preferably the permeant of interest is formulated in the semi-solid and permeation of the permeant of interest is from the semi-solid through a membrane to the second liquid.

By detecting ultra-violet transmitted through or reflected from the sample spanning an area of the sample which is or includes an area of the semi-solid, this embodiment offers advantages over conventional methods in which the constitution of the semi-solid and the often high concentration of the permeant of interest would make it possible only to analyse the second liquid (receptor phase).

Particularly preferably the semi-solid is a lotion, cream, salve, liniment, embrocation, rub, gel, petroleum jelly, balm, emollient, foam, unguent or balsam containing the permeant of interest.

The semi-solid may be a formulation (eg a dosage formulation) selected from the group consisting of a pharmaceutical formulation (eg drug), cosmetic formulation, diagnostic agent formulation or biocide (eg pesticide such as fungicide, herbicide, insecticide, algicide, molluscicide, miticide and rodenticide or antimicrobial such as germicide, antibiotic, antibacterial, antiviral, antifungal, antiprotozoal or antiparasite) formulation.

The semi-solid may be a medical formulation (eg a pharmaceutical or veterinary formulation). The medical formulation may be adapted for topical administration (eg administration to the skin or mucous membrane). For example, the medical formulation may be used for epicutaneous, inhalational, aural, dental, vaginal, rectal, buccal, ocular or nasal administration.

Preferably the semi-solid is a medical formulation for trans-dermal delivery.

The second liquid may be a physiological fluid simulant such as phosphate buffered saline (PBS) optionally together with alcohols, surfactants, liposomes or proteins (eg serum albumin).

The advantages of the method of the invention will allow development and screening of potential formulations to be carried out much more effectively and at lower cost. This in turn will allow improved technical and commercial decisions to be made earlier in the development cycle which will lead to better formulations getting to market sooner. The method will substantially reduce the need for animal and human tissue testing of potential new formulations.

The membrane may be a natural (eg biological) membrane. The membrane may be animal tissue (eg mammalian or non-mammalian tissue). The membrane may be human tissue (eg cadaver or non-cadaver tissue), non-human animal tissue (eg rat or pig tissue) or tissue construct.

The membrane may be a synthetic membrane. The membrane may be a synthetic polymer membrane.

Preferably the membrane is a tissue simulant (eg a human tissue simulant). For example, the membrane may be a simulant of skin, ocular tissue or gastrointestinal tissue. Tissue simulants are available commercially and include a living skin equivalent LabSkin™ (Evocutis PLC), Apligraf™ (Graftskin) and Strat-M™ (EMD Millipore).

Preferably the membrane is a simulant of skin (eg human skin) or a part thereof (eg the epidermis). In this embodiment, the characteristic of permeation is advantageously structural or mechanistic (eg lateral and transverse skin penetration routes or pathways such as an intercellular, transcellular, intrafollicular or polar pathways or penetration via sebaceous glands). In this embodiment, the semi-solid may include a penetration enhancer such as an enzyme, chemical enhancer, vesicle or ceramide.

The permeation of the permeant of interest may be between a first liquid and a second liquid. The permeation of the permeant of interest may be from the first liquid to the second liquid. The permeation of the permeant of interest may be from the second liquid to the first liquid. By way of example, the first liquid may be organic and the second liquid may be aqueous.

The membrane may permit permeation of one or more first permeants from the first liquid to the second liquid and of one or more second permeants from the second liquid to the first liquid. In this embodiment, the characteristic of permeation may be partition. The representation of the characteristic of permeation may be a partition coefficient.

Where permeation of the permeant of interest is between the first liquid and the second liquid, the membrane may have a first face which is hydrophobic and a second opposed face which is hydrophilic. Membranes of this type may be commercially available and include Accurel (Bend Research).

The source of ultra-violet irradiation may be a light (UV) emitting diode (eg 255 nm). The source of visible irradiation may be a light (VIS) emitting diode (eg 505 nm). A light (UV) emitting diode and a light (VIS) emitting diode may be switched sequentially to alternate between incident UV and VIS irradiation.

The source of ultra-violet irradiation and optics may include a collimator for generating collimated ultra-violet irradiation along a path of incident ultra-violet irradiation.

The source of ultra-violet irradiation may be a deuterium or pulsed xenon source (eg a flash lamp). A pulsed xenon source may be used with an oscillating filter holder to alternate between incident UV and VIS irradiation.

The source of ultra-violet irradiation is typically capable of generating ultra-violet irradiation of at least one wavelength absorbed by the permeant of interest. Typically the source of ultra-violet irradiation operates in the range 180 to 1200 nm.

The ultra-violet area detector may comprise a plurality of individual detector elements. The ultra-violet area detector may comprise an active pixel sensor array.

Viewed from a further aspect the present invention provides a sample assembly for containing a sample of a first liquid or semi-solid and a second liquid to facilitate the permeation of a permeant of interest between the first liquid or semi-solid and the second liquid across an interface therebetween, wherein the permeant of interest is formulated in either the first liquid or semi-solid or in the second liquid, wherein the sample assembly comprises:

an elongate receptor cell for the second liquid;
an elongate cuvette which is axially insertable or inserted into the elongate receptor cell, wherein the elongate cuvette has a lower insertion end which delimits the interface;
an elongate substantially planar holder for the semi-solid or first liquid which comprises a main elongate planar body which is non-transmissive to ultra-violet and visible irradiation and which terminates at its lower end in a pair of parallel spaced apart planar legs, wherein on a front and rear face of the pair of parallel spaced apart planar legs is mounted respectively a pair of windows which is transmissive to ultra-violet and visible irradiation, wherein the pair of parallel spaced apart planar legs and pair of windows together bound a chamber for the semi-solid or first liquid, wherein the elongate substantially planar holder is axially insertable or inserted in the elongate cuvette such that a foot of each of the pair of parallel spaced apart planar legs is substantially coincident with the interface, wherein in use the sample assembly is positioned downstream in a path of incident ultra-violet irradiation such that there is a path length throughout an area of the sample which is or includes an area of the first liquid or semi-solid or of the second liquid in which the permeant of interest is formulated.

Each of the elongate receptor cell and elongate cuvette may be substantially cuboidal. The incident face of each of the elongate receptor cell and elongate cuvette may be quadrilateral (eg rhombic such as rectangular). Typically each of the elongate receptor cell and elongate cuvette is composed of quartz, glass or plastic.

In the elongate receptor cell, the second liquid is fixed volume.

Preferably the elongate substantially planar holder is axially insertable or inserted in the elongate cuvette so as to project beyond an upper end of the elongate cuvette which is opposite the lower insertion end.

Preferably the pair of windows is mounted on a lower part of the front and rear face of the pair of parallel spaced apart planar legs to leave exposed an upper part of the front and rear face of the pair of parallel spaced apart planar legs.

The elongate receptor cell is typically configured to be mounted snugly (eg dismountably mounted snugly) in the path of incident ultra-violet irradiation in or adjacent to the ultra-violet area detector. For example, the elongate receptor cell may be mounted snugly in a cartridge of the ultra-violet area detector or attached thereto.

The sample assembly may be multiplexed. For example, the sample assembly may comprise a plurality of each of the elongate receptor cell, elongate cuvette and elongate substantially planar holder as hereinbefore defined, wherein the plurality of elongate receptor cells is mounted snugly in a carousel of the ultra-violet area detector or attached thereto.

Preferably the interface is a membrane and the elongate cuvette is capped at the lower insertion end with the membrane.

Preferably the elongate receptor cell is equipped with a device for agitating the second liquid. The device may be a mechanical or ultrasound device. The device may be a stirrer. Typically the device is positioned substantially beneath the interface.

The sample assembly may be adapted to apply an electric field to the sample to promote permeation. For example, the elongate receptor cell may be equipped with an electrode arrangement for applying an electric field to the sample (eg the second liquid) to promote permeation.

The elongate cuvette may be slidably insertable or inserted into the elongate receptor cell.

The elongate cuvette may be withdrawably insertable or inserted into the elongate receptor cell.

The elongate substantially planar holder may be slidably insertable or inserted in the elongate cuvette.

The elongate substantially planar holder may be withdrawably insertable or inserted in the elongate cuvette.

Viewed from a yet further aspect the present invention provides a system for generating a representation of a characteristic of the permeation of a permeant of interest between a first liquid or semi-solid and a second liquid across an interface therebetween, wherein the permeant of interest is formulated in either the first liquid or semi-solid or in the second liquid, wherein the system comprises:

a source of ultra-violet irradiation which is capable of generating ultra-violet irradiation along a path of incident ultra-violet irradiation;

a sample assembly as hereinbefore defined for containing a sample of the first liquid or semi-solid and the second liquid positioned downstream in the path of incident ultra-violet irradiation such that there is a path length throughout an area of the sample, wherein the area of the sample is or includes an area of the first liquid or semi-solid or of the second liquid in which the permeant of interest is formulated;

an ultra-violet area detector for detecting ultra-violet irradiation transmitted through or reflected from the sample spanning the area of the sample; and means for manipulating the ultra-violet irradiation transmitted through or reflected from the sample spanning the area of the sample into the representation of a characteristic of the permeation.

Preferably the source of ultra-violet irradiation is a source of ultra-violet and visible irradiation capable of generating visible irradiation along a path of incident visible irradiation and the ultra-violet area detector is an ultra-violet and visible area detector.

Alternatively preferably the system further comprises:

a source of visible irradiation which is capable of generating visible along a path of incident visible irradiation, wherein the source of visible irradiation is separate from the source of ultra-violet irradiation; and a visible area detector.

Viewed from a still yet further aspect the present invention provides an elongate substantially planar holder as hereinbefore defined.

Viewed from an even still yet further aspect the present invention provides the use of an elongate substantially planar holder as hereinbefore defined in generating a representation of a characteristic of the permeation of a permeant of interest from a semi-solid formulation of the permeant of interest into in vivo tissue.

Viewed from a furthest aspect the present invention provides a process for generating a representation of a characteristic of the permeation of a permeant of interest from a semi-solid formulation of the permeant of interest into in vivo tissue, wherein the process comprises:

(a) charging the chamber of an elongate substantially planar holder as hereinbefore defined with a sample of the semi-solid formulation of the permeant of interest;

(b) applying the foot of each of the pair of parallel spaced apart planar legs of the elongate substantially planar holder to the in vivo tissue for a period of time;

(c) providing a source of ultra-violet irradiation which is capable of generating ultra-violet irradiation along a path of incident ultra-violet irradiation;

(d) positioning the elongate substantially planar holder downstream in the path of incident ultra-violet irradiation such that there is a path length throughout an area of the sample;

(e) generating ultra-violet irradiation from the source of ultra-violet irradiation along the path of incident ultra-violet irradiation whereby the incident ultra-violet irradiation is incident on the area of the sample;

(f) detecting ultra-violet irradiation transmitted through or reflected from the sample spanning the area of the sample using an ultra-violet area detector; and (g) manipulating the ultra-violet irradiation transmitted through or reflected from the sample spanning the area of the sample into the representation of a characteristic of the permeation.

In the further and furthest aspects of the invention, features in common with the first aspect of the invention are as hereinbefore defined.

Figure 2A:
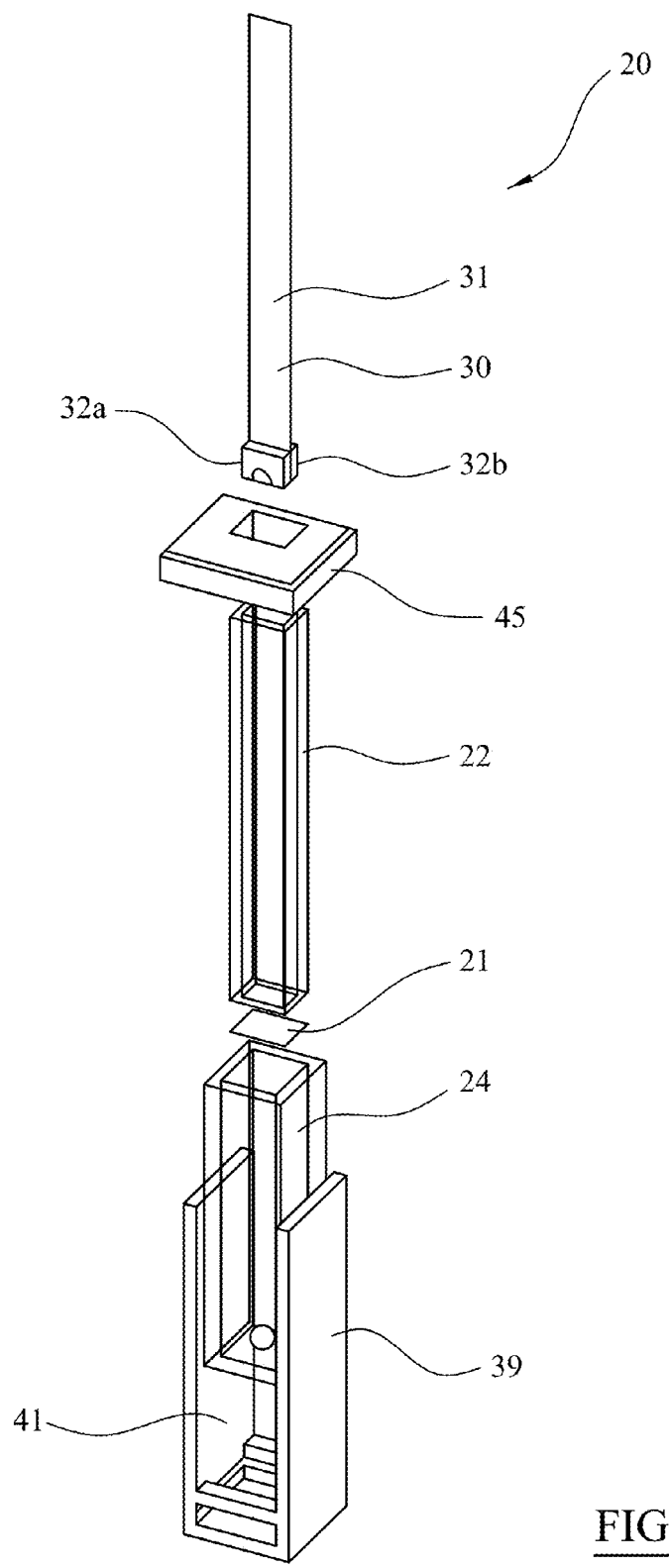
Figure 2B:
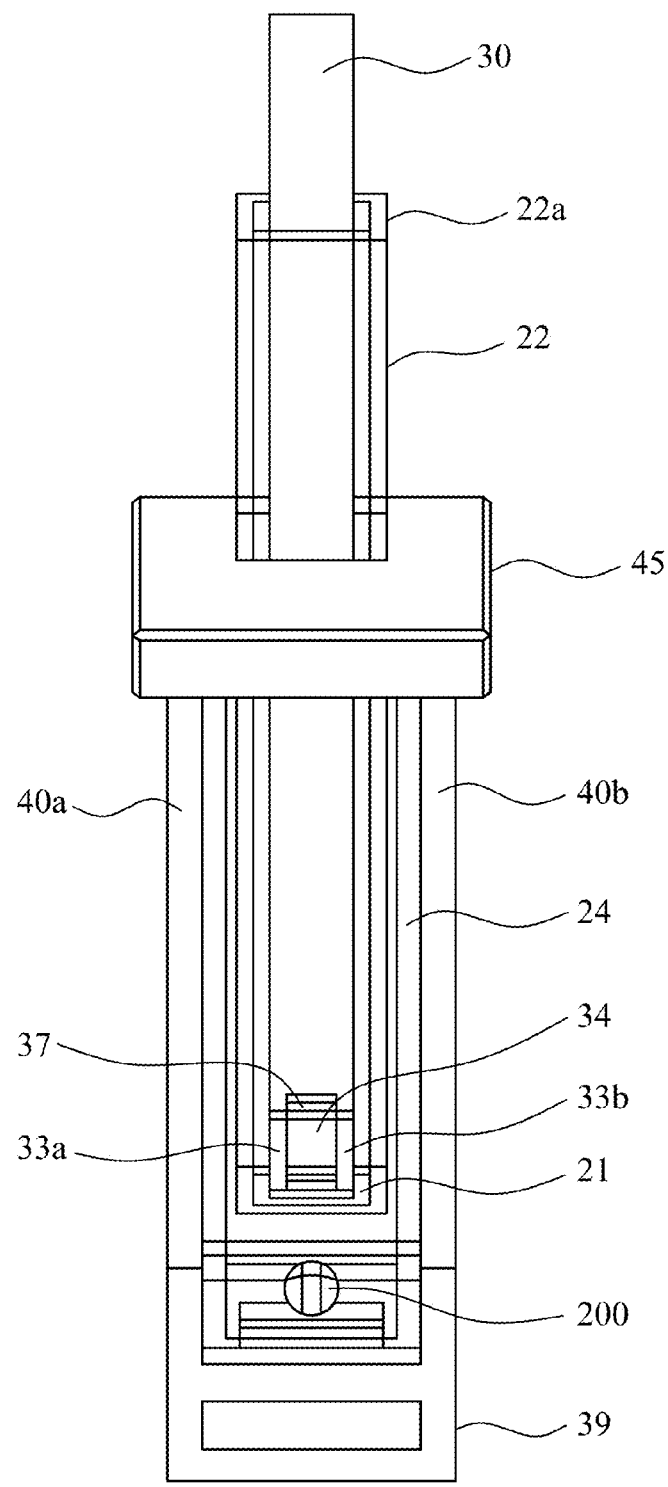
Figure 3A:
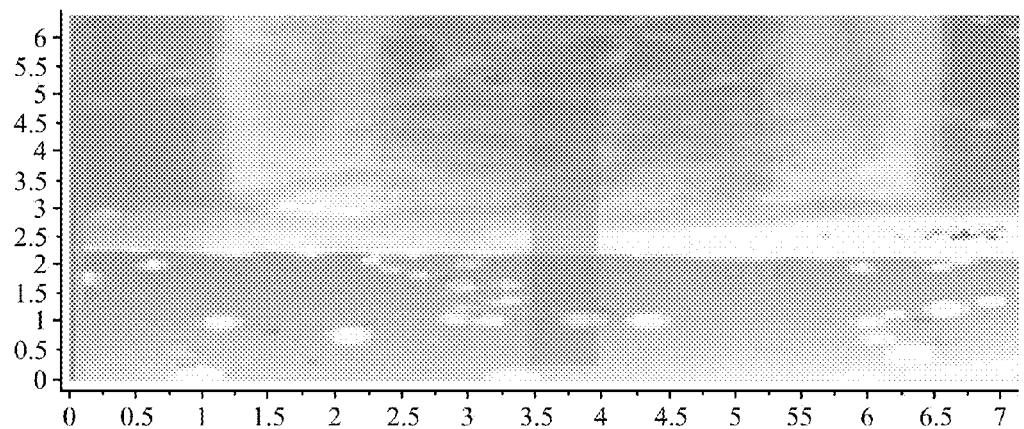
Figure 3B:
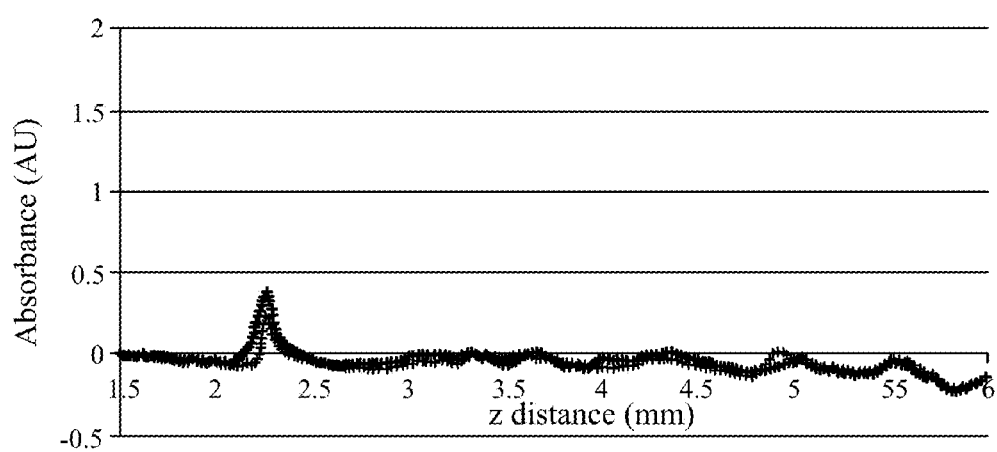

The present invention will now be described in a non-limitative sense with reference to Examples and the accompanying Figures in which:

FIG. 1: A schematic illustration of a first embodiment of the system of the invention;

FIG. 2: A detailed (a) exploded view and (b) front view of a sample assembly used in the system of the invention;

FIG. 3A: The portion of an image spanning the membrane and the centre of the sample assembly. The vertical bar (z direction) is used for measurement of the absorbance profile;

FIG. 3B: VIS absorbance as function of z distance at 61 minutes (light) and 331 minutes (dark).

Figure 3C:
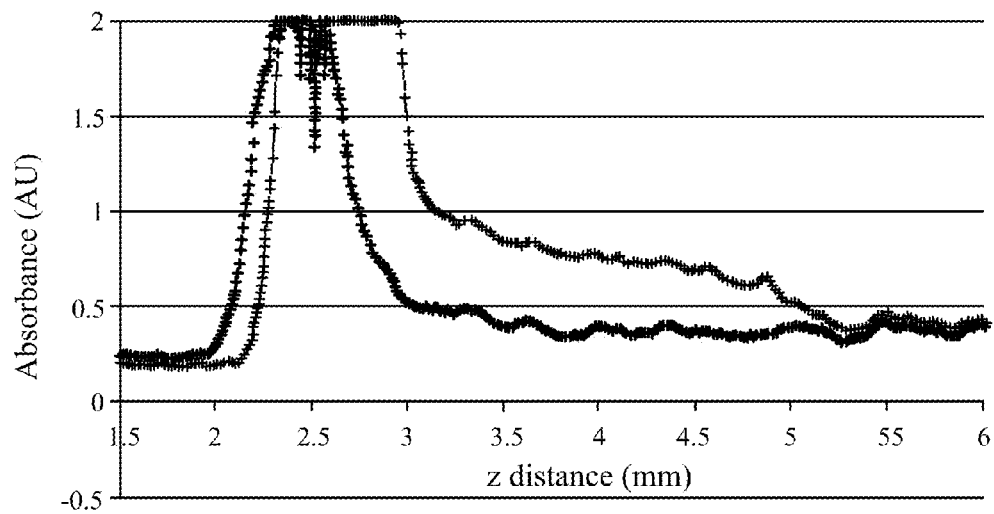

FIG. 3C: UV absorbance as function of z distance at 61 minutes (light) and 331 minutes (dark).

Figure 3D:
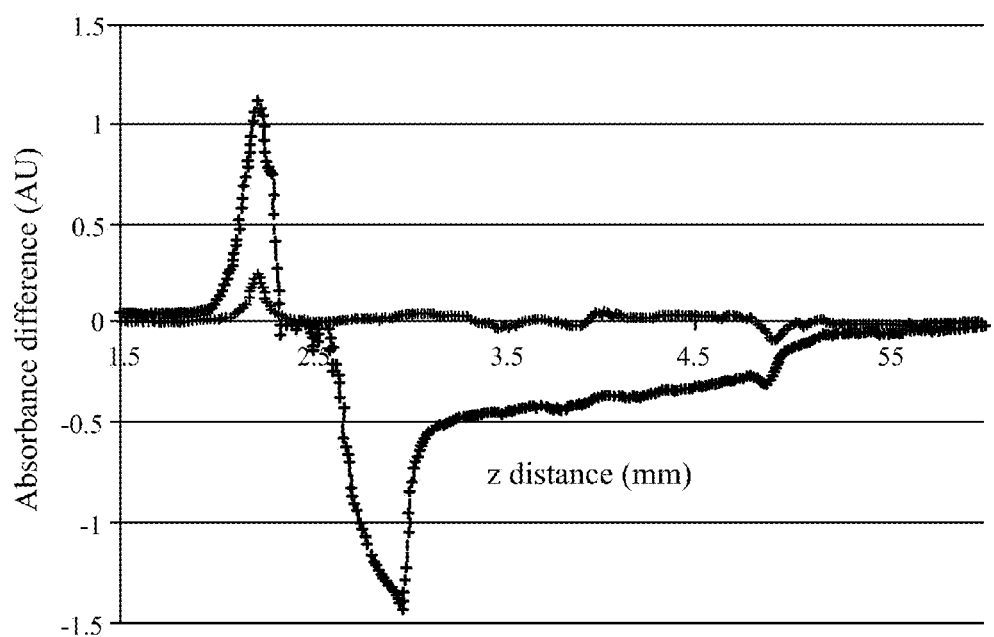
Figure 4:
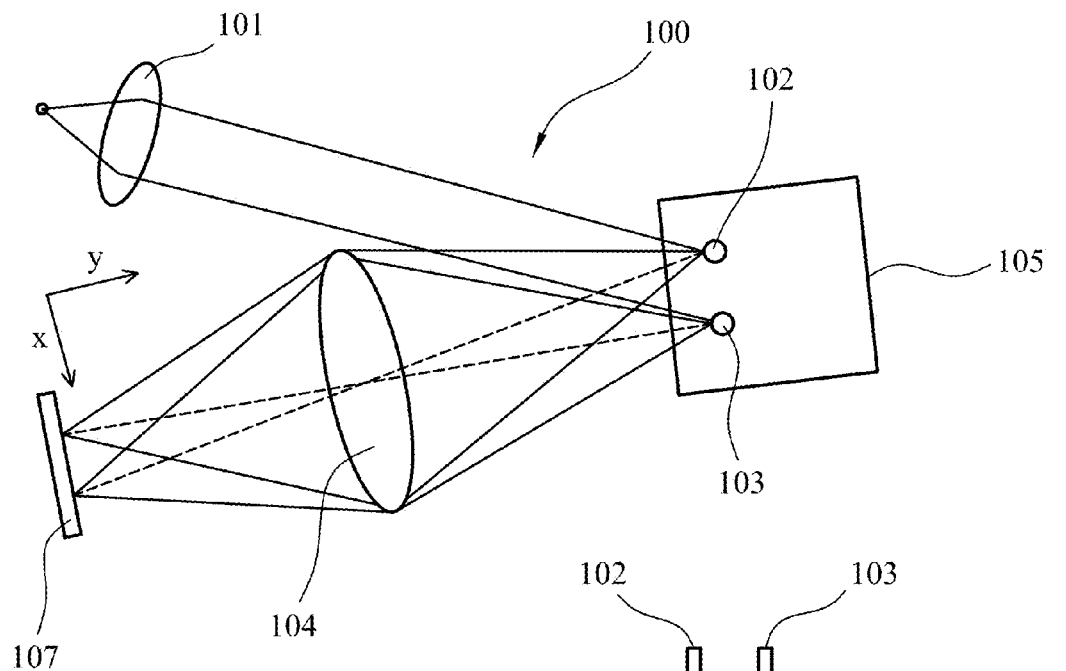
Figure 4:
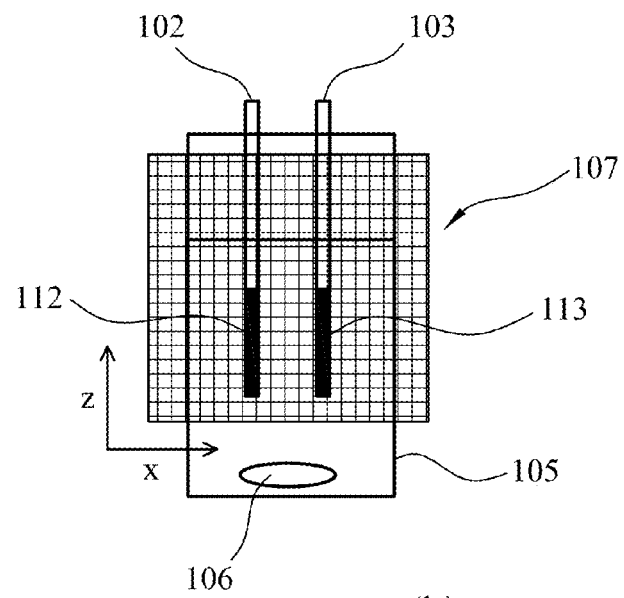

FIG. 3D: Difference absorbance 331–61 minutes as function of z distance for UV (dark) and VIS (light);

FIG. 4: A schematic illustration of a second embodiment of the system of the invention in (a) the x-y plane and (b) the x-z plane; and FIG. 5: The arrangement of the sources of irradiation in the first embodiment.

EXAMPLE 1

Figure 5:
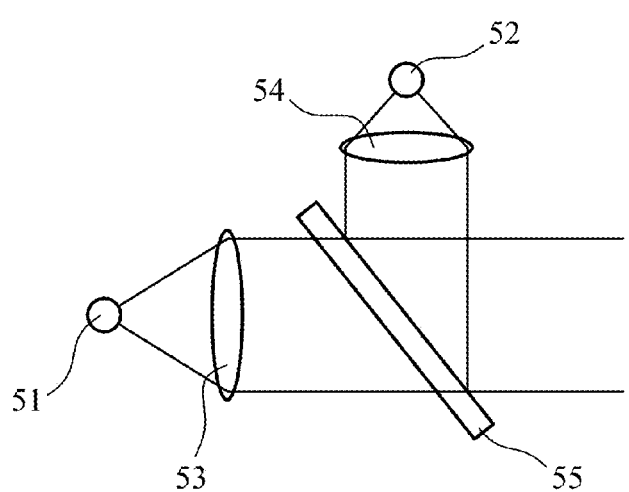

FIG. 1 is a schematic illustration of a first embodiment of the system of the invention designated generally by reference numeral 1. The system 1 has an LED source of UV irradiation, an LED source of VIS irradiation and accompanying optics 2 alternately generating collimated UV and VIS irradiation 10 incident on a front rectangular face 3 of an elongate receptor cell 4. Shown in detail in FIG. 5 are the LED source of UV irradiation 51, a fused silica lens 53, the LED source of VIS irradiation 52, a lens 54 and a fused silica plate beamsplitter 55 inclined at 45 degrees to the direction of the irradiation 10 which are housed in an optics block 90 (shown in the insert of FIG. 1). Measurements were made by switching the LED source of UV irradiation 51 and the LED source of VIS irradiation 52 and imaging at a frame rate of 2 Hz.

The elongate receptor cell 4 contains a receptor liquid 14 (~2 mL—the "receptor phase") such as a phosphate buffered saline solution. An API formulation 13 (~1 µL—the "donor phase") is contained in a UV-transparent fused silica elongate cuvette 12 capped with a membrane 11. The elongate receptor cell 4 and fused silica elongate cuvette 12 are part of a sample assembly 20 described in detail below with reference to FIG. 2.

An area imaging detector 7 is close coupled to a rear face 5 of the elongate receptor cell 4. The imaging area detector 7 spans the receptor liquid 14 and the UV-transparent fused silica elongate cuvette 12 containing the API formulation 13.

The rate of transfer of the API from the API formulation 13 to the receptor liquid 14 may be obtained by imaging API depletion propagating into the API formulation 13 and optionally imaging API accumulation in the receptor liquid 14. Imaging is typically carried out alternately at a first wavelength where the API absorbs light (280 or 255 nm) and a second wavelength where there is no absorption (505 nm).

FIG. 2 is a detailed (a) exploded view and (b) front view of a sample assembly 20 which is used in the system of the invention 1. The sample assembly 20 comprises an elongate receptor cell 24 of fused silica which is cuboidal with a width and depth of 10 mm (the optical path) and a wall thickness of 1 mm. The vertical dimension is 4.5 cm. The sample assembly 20 further comprises a fused silica elongate cuvette 22 which is cuboidal and open at the upper end with a width of 7 mm, a depth of 4 mm and a wall thickness of 1 mm. The vertical dimension is 8 cm. The fused silica elongate cuvette 22 is inserted vertically inside the elongate receptor cell 24 and is capped at a lower end with a membrane 21 which is glued in place. Mounted on an intermediate exterior circumference of the fused silica elongate cuvette 22 is an exterior skirt 45 which is positioned judiciously to cap the upper end of the elongate receptor cell 24.

A miniature stir bar driver is fitted in a lower part of the chamber of the elongate receptor cell 24 directly beneath the fused silica elongate cuvette 22 allowing the receptor liquid 14 to be stirred with a stir bar 200. In an alternative embodiment, the sample assembly 20 may be equipped with tubing for flowing or recirculating the receptor liquid 14.

The sample assembly 20 further comprises an elongate substantially planar holder 30 for the API formulation 13 (the donor phase) which is slidably inserted in the fused silica elongate cuvette 22. The elongate substantially planar holder 30 projects beyond an upper end 22a of the fused silica elongate cuvette 22 to facilitate removal. A main elongate body 31 of the elongate substantially planar holder 30 (width 5 mm) is non-transmissive to UV and VIS (eg plastic) and terminates at its lower end in a pair of parallel spaced apart planar legs 33a, b (width 1 mm). Mounted on a lower part of the front and rear face of the pair of parallel spaced apart planar legs 33a, b is a pair of fused silica windows 32a, 32b (width and height of 5 mm and depth of 1 mm) so as to leave a gap 37. The pair of parallel spaced apart planar legs 33a, b and pair of fused silica windows 32a, 32b together bound a donor chamber 34 which is transmissive to UV and VIS. The donor chamber 34 is loaded with the API formulation 13 either by pre-loading or by transfer from a positive displacement pipette. The elongate substantially planar holder 30 is axially inserted into the fused silica elongate cuvette 22 such that a foot of each of the pair of parallel spaced apart planar legs 33a, 33b is substantially coincident with the membrane 21 which is then between the receptor liquid 14 and API formulation 13. In an alternative embodiment, the fused silica elongate cuvette 22 is uncapped and the lower end serves to delimit an interface between the receptor liquid 14 and the API formulation 13.

In use, the sample assembly 20 is slidably mounted in a cartridge 39 so that at least the donor chamber 34 is in the path of the incident irradiation. The cartridge 39 may be a part of the area imaging detector 7 or attached to it. The cartridge 39 comprises a pair of spaced apart planar walls 40a, b between which is defined a transverse passage 41 for receiving the sample assembly 20. The transverse passage 41 is coincident with the optical axis. The elongate receptor cell 24 is snugly engaged with the inner surface of the pair of spaced apart planar walls 40a, b. The skirt 45 is seated on the upper end of the cartridge 39.

The following are examples of tests that have been carried out with the system of the invention.

(1) Release of Tetracaine from PEG Formulations.

Tetracaine which is a local anaesthetic was present in a donor phase containing polyethylene glycol (PEG) and permeation was through a silicone membrane (a synthetic skin substitute) into water as the receptor phase.

(2) Release of Ketoprofen from Agarose Gels.

Ketoprofen which is a non-steroidal anti-inflammatory drug was released from a gel donor phase with a direct interface to phosphate buffered saline (PBS) as the receptor phase. Depletion of ketoprofen in the donor phase as well as enrichment in the receptor phase was clearly visible by imaging.

In tests (1) and (2), the benefits of carrying out imaging at two wavelengths were demonstrated. Studies were carried out over 1 hour to allow build-up of a quasi-steady state at the interface and for permeation to be compared in both unstirred and stirred conditions. Data were collected at a frame rate of ~1 Hz giving data points at 1 s intervals. It was found that sufficiently high-quality data could be gathered in real time over a period of minutes. This is a significant improvement on the 6 hours currently required for standard IVRT measurements.

(3) Rapid In Vitro Release Testing of Ibuprofen Gel

In this Example using the system and sample chamber described above with reference to FIGS. 1 and 2, the area imaging detector 7 was an ActiPix™ D100 detector system and irradiation was carried out alternately at 255 nm (UV) and 505 nm (VIS) by LEDs at ~1 Hz repetition rate. Using a positive displacement pipette, 1 µL 5% ibuprofen gel (Boots plc, UK) was inserted into the donor chamber 34 of the narrow elongate substantially planar sample holder 30 (200 µm optical path length) with fused silica windows 32a, 32b. The elongate substantially planar holder 30 was pushed down to contact a Strat-M™ membrane (EMD Millipore) glue bonded to the lower end of the rectangular fused silica cuvette 22 positioned within a standard 1 cm path length UV elongate receptor cell 24 containing 1.5 mL of a PBS receptor phase. A miniature magnetic stir-bar driver underneath the rectangular fused silica elongate cuvette 22 allowed the receptor phase to be stirred with a stir bar 200.

Results

It was found that Ibuprofen could be imaged in the UV at 255 nm and time dependent changes in its spatial distribution monitored. The visible image data tracked physical phenomena such as any changes to boundaries and movement of bubbles. FIG. 3A shows the portion of an image spanning the membrane and the centre of the sample assembly. The vertical bar (z direction) was used for measurement of the absorbance profiles spanning the donor phase, the membrane and the receptor phase (see FIGS. 3B to D).

Absorbance profiles along a zone (A) at two times (61 and 331 minutes) showed no change in the VIS (B) but a substantial change in the UV (C). Changes were quantified by difference absorbance 331–61 minutes (D) in the UV: in the donor phase with minimum −1.4 AU; in the receptor phase, there was an increase with maximum 1.1 AU directly under the membrane. In the bulk receptor phase there was an increase of 0.045 AU. The depletion value of the donor phase is in good agreement with a value −1.5 AU calculated from the path length, the ibuprofen concentration in the gel and the literature value of extinction coefficient (1.5 dm$^3$ g$^{-1}$ cm$^{-1}$). The increased value in the receptor phase agrees well with the value 0.05 AU expected from ibuprofen diluted from 5% w/w by the 1:1500 volume ratio of the donor phase:receptor phase.

Conclusion

Imaging through a thin layer of a semi-solid allows direct probing of depletion during transfer of a drug across a membrane simulating transdermal skin permeation.

EXAMPLE 2

FIG. 4 is a schematic illustration of an embodiment of the system of the invention designated generally by reference numeral 100 in (a) the x-y plane and (b) the x-z plane. The system 100 has a UV diode source and accompanying optics 101 irradiating a sample cell 102 and reference cell 103 mounted in a receptor chamber 105. The sample cell 102 is charged with a donor phase containing an API of interest 112. The reference cell 103 is charged with the donor phase 113 containing no API. The receptor chamber 105 is charged with a phosphate buffered saline solution (the receptor phase) and is equipped with a stirrer 106.

The UV reflectance passes through a UV lens 104 to a UV area detector (eg active pixel sensor) 107 which is positioned to detect reflectance from an area including the donor phase containing the API of interest 112, the donor phase 113 containing no API and reference areas above them.

The invention claimed is:

1. A system for generating a representation of a characteristic of the permeation of a permeant of interest between a first liquid or semi-solid and a second liquid across an interface therebetween, wherein the permeant of interest is formulated in either the first liquid or semi-solid or in the second liquid, wherein the system comprises:
  a source of ultra-violet irradiation which is capable of generating ultra-violet irradiation along a path of incident ultra-violet irradiation;
  a sample assembly for containing a sample of the first liquid or semi-solid and the second liquid positioned downstream in the path of incident ultra-violet irradiation such that there is a path length throughout an area of the sample, wherein the area of the sample is or includes an area of the first liquid or semi-solid or of the second liquid in which the permeant of interest is formulated, wherein the sample assembly comprises:
    an elongate receptor cell for the second liquid;
    an elongate cuvette which is axially insertable or inserted into the elongate receptor cell, wherein the elongate cuvette has a lower insertion end which delimits the interface; and
    an elongate substantially planar holder for the semi-solid or first liquid which comprises a main elongate planar body which is non-transmissive to ultra-violet and visible irradiation and which terminates at its lower end in a pair of parallel spaced apart planar legs, wherein on a front and rear face of the pair of parallel spaced apart planar legs is mounted respectively a pair of windows which is transmissive to ultra-violet and visible irradiation, wherein the pair of parallel spaced apart planar legs and pair of windows together bound a chamber for the semi-solid or first liquid, wherein the elongate substantially planar holder is axially insertable or inserted in the elongate cuvette such that a foot of each of the pair of parallel spaced apart planar legs is substantially coincident with the interface;
  an ultra-violet area detector for detecting ultra-violet irradiation transmitted through or reflected from the sample spanning the area of the sample; and
  means for manipulating the ultra-violet irradiation transmitted through or reflected from the sample spanning the area of the sample into the representation of a characteristic of the permeation.

2. A system as claimed in claim 1 wherein the elongate substantially planar holder is axially insertable or inserted in the elongate cuvette so as to project beyond an upper end of the elongate cuvette which is opposite the lower insertion end.

3. A system as claimed in claim 1 wherein the pair of windows is mounted on a lower part of the front and rear face of the pair of parallel spaced apart planar legs to leave exposed an upper part of the front and rear face of the pair of parallel spaced apart planar legs.

4. A system as claimed in claim 1 wherein the interface is a membrane and the elongate cuvette is capped at the lower insertion end with the membrane.

5. A process for generating a representation of a characteristic of the permeation of a permeant of interest from a semi-solid formulation of the permeant of interest into in vivo tissue, wherein the process comprises:
  (a) charging the chamber of an elongate substantially planar holder with a sample of the semi-solid formulation of the permeant of interest, wherein the elongate substantially planar holder comprises a main elongate planar body which is non-transmissive to ultra-violet and visible irradiation and which terminates at its lower end in a pair of parallel spaced apart planar legs, wherein on a front and rear face of the pair of parallel spaced apart planar legs is mounted respectively a pair of windows which is transmissive to ultra-violet and visible irradiation, wherein the pair of parallel spaced apart planar legs and pair of windows together bound a chamber for the semi-solid formulation of the permeant of interest;
  (b) applying the foot of each of the pair of parallel spaced apart planar legs of the elongate substantially planar holder to the in vivo tissue for a period of time;
  (c) providing a source of ultra-violet irradiation which is capable of generating ultra-violet irradiation along a path of incident ultra-violet irradiation;
  (d) positioning the elongate substantially planar holder downstream in the path of incident ultra-violet irradiation such that there is a path length throughout an area of the sample;
  (e) generating ultra-violet irradiation from the source of ultra-violet irradiation along the path of incident ultra-violet irradiation whereby the incident ultra-violet irradiation is incident on the area of the sample;
  (f) detecting ultra-violet irradiation transmitted through or reflected from the sample spanning the area of the sample using an ultra-violet area detector; and
  (g) manipulating the ultra-violet irradiation transmitted through or reflected from the sample spanning the area of the sample into the representation of a characteristic of the permeation.

\* \* \* \* \*